(12) United States Patent
Kishimoto et al.

(10) Patent No.: US 7,718,426 B2
(45) Date of Patent: May 18, 2010

(54) PREPARATION METHOD OF A HAIR DERMAL PAPILLA CELL PREPARATION, COMPOSITION AND METHOD FOR REGENERATING HAIR FOLLICLES, AND ANIMAL HAVING REGENERATED HAIR FOLLICLES

(75) Inventors: Jiro Kishimoto, Yokohama (JP); Ritsuko Ehama, Yokohama (JP); Ritsuro Ideta, Yokohama (JP); Takayuki Arai, Yokohama (JP); Kiichiro Yano, Yokohama (JP); Tsutomu Soma, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 313 days.

(21) Appl. No.: 10/574,697

(22) PCT Filed: Sep. 30, 2004

(86) PCT No.: PCT/JP2004/014779

§ 371 (c)(1),
(2), (4) Date: Apr. 5, 2006

(87) PCT Pub. No.: WO2005/033302

PCT Pub. Date: Apr. 14, 2005

(65) Prior Publication Data

US 2007/0122386 A1 May 31, 2007

(30) Foreign Application Priority Data

| Oct. 6, 2003 | (JP) | ............................... 2003-346937 |
| Oct. 6, 2003 | (JP) | ............................... 2003-346939 |
| Feb. 24, 2004 | (JP) | ............................... 2004-048322 |

(51) Int. Cl.
*C12N 5/10* (2006.01)
*A01N 65/00* (2006.01)
*C12N 5/07* (2010.01)

(52) U.S. Cl. ...................... 435/347; 424/93.7; 435/353; 435/354; 435/366; 435/371

(58) Field of Classification Search ........................ None
See application file for complete search history.

(56) References Cited

U.S. PATENT DOCUMENTS

| 4,888,291 A * | 12/1989 | Barrandon et al. ......... 424/93.7 |
| 5,851,831 A * | 12/1998 | Inamatsu et al. ............ 435/383 |
| 6,521,635 B1 * | 2/2003 | Bates et al. ................. 514/297 |

FOREIGN PATENT DOCUMENTS

WO WO 01/70021 9/2001

OTHER PUBLICATIONS

Ehama, Ritsuko, et al., "Reconstitution of chimeric hair follicle from human-derived cells" The Molecular Biology Society of Japan Nenkai, Nov. 2003, vol. 26, frame 2PC-024, p. 764 (English title only).*
Ehama, R. et al. "Hair follicle Regeneration Using Grafted Rodent and human Cells" Journal of Investigative Dermatology. 2007, 127, 2106-2115.*
Chuong, C-M, Costarelis, G., Stenn, K. "Defining Hair Follicles in the Age of Stem Cell Bioengineering", Journal of Investigative Dermatology, 2007, 127, 2098-2100.*
Stenn, K.S., et al. "Phylogeny of the Hair Follicle: The Sebogenic Hypothesis", Journal of Investigative Dermatology, 2008, vol. 128, pp. 1-3 (published online Dec. 13, 2007).*
Amano, Satoshi et al., "Importance of Balance between Extracellular Matrix Synthesis and Degradation in Basement Membrane Formation," Experimental Cell Research, 2001, pp. 249-262, vol. 271.
Kishimoto, Jiro et al., "Selective Activation of the Versican Promoter by Epithelial-Mesenchymal Interactions During Hair Follicle Development," Proc. Natl. Acad. Sci., Jun. 1999, pp. 7336-7341, vol. 96.
Prouty, Stephen M. et al., "Fibroblast-Dependent Induction of a Murine Skin Lesion with Similarity to Human Common Blue Nevus," American Journal of Pathology, Jun. 1996, pp. 1871-1885, vol. 148, No. 6.
Weinberg, Wendy C. et al., "Reconstitution of Hair Follicle Development In Vivo: Determination of Follicle Formation, Hair Growth, and Hair Quality by Dermal Cells," The Journal of Investigative Dermatology, 1993, pp. 229-236, vol. 100.
Miller, Gary J. and Ferrara, Janet A., "Identification of mormal or Neoplastic Murine Mesenchymal Cells in Chimeric Tissues or Heterotransplants," Stain Technology, 1988, pp. 15-21, vol. 63, No. 1.
Reynolds, Amanda J. et al., "Hair follicle stem cells? A distinct germinative epidermal cell population is activated in vitro by the presence of hair dermal papilla cells", Journal of Cell Science, Jun. 1991, pp. 373-385, vol. 99.
Jinjin et al., "An Efficient Method for Isolation and Cultivation of Human Scalp Dermal Papilla Cells," Journal of Chinese Dermatology, vol. 30:383-385 (1997).
Yuan-gang et al., "Study on Freezing Storage of Human Dermal Papilla Cells," Journal of Chongqing Unviversity (Natural Science Edition), vol. 25:48-50 (2002).

* cited by examiner

Primary Examiner—Christopher R Tate
Assistant Examiner—Aaron J Kosar
(74) Attorney, Agent, or Firm—Fish & Richardson P.C.

(57) ABSTRACT

The present invention provides a method for preparing a hair dermal papilla cell preparation comprising preparing a cell suspension by removing epidermal tissue from skin tissue and subjecting the resulting dermal tissue fraction to collagenase treatment, and cyropreserving the cell suspension to kill the follicular epidermal cells. The present invention also provides a composition for regenerating hair follicles comprising hair dermal papilla cell and epidermal cells, wherein the ratio of the number of hair dermal papilla cell to the number of epidermal cells is from 1:10 to 10:1.

9 Claims, 6 Drawing Sheets

Fig.3

Fig.5
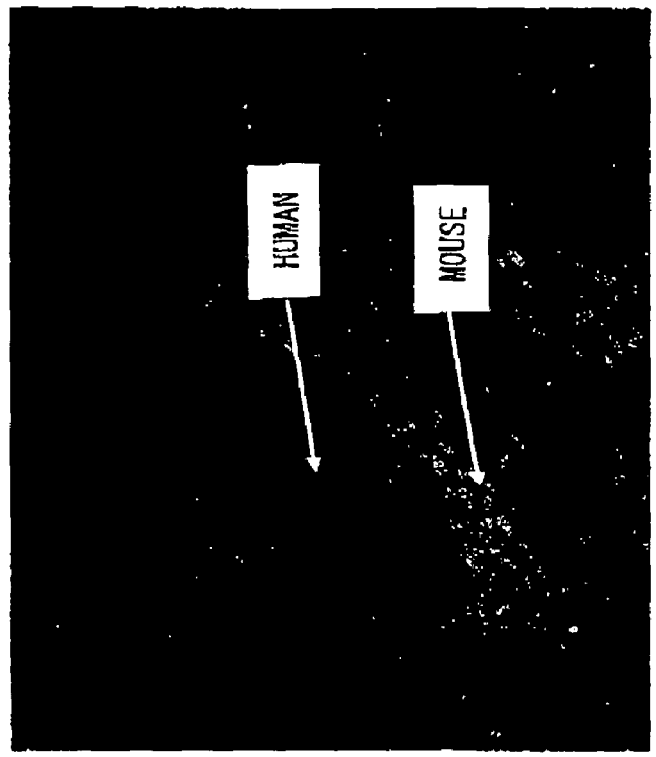
HOECHST NUCLEAR STAINING
TISSUE IMAGE

Fig.6
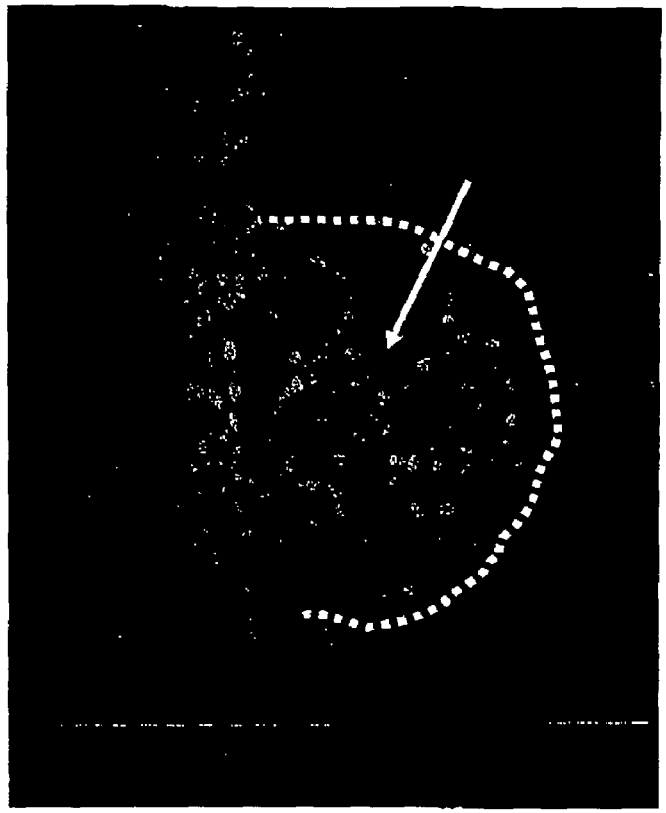
HOECHST NUCLEAR STAINING
HUMAN FIBROBLASTS+HUMAN EPITHELIAL CELLS
+MOUSE HAIR PAPILLA CELL FRACTION

PREPARATION METHOD OF A HAIR DERMAL PAPILLA CELL PREPARATION, COMPOSITION AND METHOD FOR REGENERATING HAIR FOLLICLES, AND ANIMAL HAVING REGENERATED HAIR FOLLICLES

TECHNICAL FIELD

The present invention provides a method for preparing a hair dermal papilla cell preparation containing active hair dermal papilla cell and in which epidermal cells contained therein are deactivated, a composition containing hair dermal papilla cell and epidermal cells for regenerating hair follicles, a method for regenerating hair follicles using the same, and an animal or three-dimensional skin equivalent having hair follicles regenerated by such a method.

BACKGROUND ART

Hair follicles are exceptional organs that repeatedly self-regenerate in a mature body throughout nearly the entire lifetime. Elucidation of the mechanism of this self-regeneration is expected to lead to clinical applications for which there are considerable needs, including hair loss therapy by tissue and cell transplant, and the construction of natural and functionally superior hair sheets containing hair follicles and sebaceous glands. Accompanying the growing interest in stem cell research in recent years, research on follicular epithelial stem cells (epidermal cells) has progressed rapidly, and the properties of hair dermal papilla cell serving as mesenchymal cells specific to hair follicles have gradually been determined. Hair dermal papilla cell fulfill the role of a so-called control tower, sending out activating signals to follicular epithelial stem cells for self-regenerating hair follicles, and have been determined to be indispensable along with follicular epithelial stem cells in evaluation of follicle reconstitution (Kishimoto et al., Proc. Natl. Acad. Sci. USA (1999); Vol. 96, pp. 7336-7341).

Hair follicle reconstitution experiments in animal models have been conducted using various methods for the purpose of hair follicle regeneration. Weinberg et al., J. Invest. Dermatol. (1993), Vol. 100, pp. 229-236 describes a hair follicle reconstitution method using a cell transplant method. The transplant system of Weinberg et al. has a complex constitution consisting of hair dermal papilla cell, newborn animal epidermal cells (including follicular epithelial stem cells) as well as the addition of mouse 3T3 cells. According to the method of Weinberg et al., hair follicles are regenerated without adding newborn animal epidermal cells containing follicular epithelial stem cells to the transplant system. However, this is thought to be phenomenon that occurred due to the difficulty in completely removing undifferentiated epidermal cells (follicular epithelial stem cells) and primordial hair follicles from the dermal cell fraction. Subsequently, Kishimoto et al. (op. cit.) succeeded for the first time in isolating and purifying hair dermal papilla cell, and as a result of conducting a hair follicle reconstitution experiment according to a cell transplant method in an animal model using the isolated and purified hair dermal papilla cell, hair follicles were reorganized and hair growth was observed when a cell fraction containing a combination of hair dermal papilla cell and epidermal cells was transplanted. However, it was found that hair growth is not observed when a cell fraction that does contain either hair dermal papilla cell or epidermal cells is transplanted.

The hair dermal papilla cell purification method according to Kishimoto et al. utilizes the fact that hair dermal papilla cell have the property of specifically expressing versicans (chondroitin sulfate proteoglycans). However, it carries out isolation and concentration by using the expression of versicans by a transgenic mouse model produced using DNA in which a reporter gene is linked to a versican gene as an indicator. Thus, this method requires the production of a transgenic mouse and purification of hair dermal papilla cell by a cell sorter. A large amount of hair dermal papilla cell are required to actually regenerate hair follicles and cause hair growth in hair follicle reconstitution methods in particular (for example, 5 million cells per transplant).

Consequently, this method requires the production of a large number of transgenic mice and the long-term use of a high-speed cell sorter, thereby resulting economic problems as well as problems in terms of work time and labor. Although the isolation of hair dermal papilla cell is also described in, for example, Prouty et al., American J. Pathol. (1996) Vol. 148, No. 6, pp. 1871-1885, this method has a complex procedure due to repeated fractionation by centrifugal separation, has a low level of purity and generates a low yield.

Thus, in previous methods for purifying hair dermal papilla cell, it was difficult to acquire an amount of isolated and purified active hair dermal papilla cell sufficient for transplant, for example, and the role of active hair dermal papilla cell in the regeneration of hair follicles was unable to be completely elucidated. In particular, it has been virtually impossible with purification methods of the prior art to determine the suitable ratio of hair dermal papilla cell and epidermal cells in follicle reconstitution systems for regenerating hair follicles.

DISCLOSURE OF THE INVENTION

An object of the present invention is to provide a method for easily preparing a hair dermal papilla cell preparation containing only hair dermal papilla cell as the active cellular component without using a transgenic mouse.

The inventors of the present invention surprisingly found that, when a cell suspension of a dermal tissue fraction collected from skin tissue was cryopreserved, contaminated follicular epidermal cells in the suspension specifically died, while the majority of the hair dermal papilla cell continued to be active. As a result, it was possible to obtain a cell preparation that contains only hair dermal papilla cell as the active cellular component. In addition, since a cell preparation obtained in this manner contains only hair dermal papilla cell as the active cellular component, it can be used to determine the ratio of hair dermal papilla cell to epidermal cells effective for regenerating hair follicles. As a result, the inventors of the present invention were able to determine the ratio of hair dermal papilla cell to epidermal cells in a hair follicle reconstitution system considered to be optimum for regenerating hair follicles.

Thus, in a first aspect thereof, the present invention provides a method for preparing a hair dermal papilla cell preparation comprising: providing a cell suspension by removing epidermal tissue from skin tissue and subjecting the resulting dermal tissue fraction to collagenase treatment, and cryopreserving the cell suspension to kill the follicular epidermal cells.

Cryopreservation is preferably carried out after adjusting the cell density of the cell suspension to $1\times10^{05}$ to $1\times10^{8}$/ml. More preferably, cryopreservation is carried out at a temperature of −80° C. or lower in, for example, liquid nitrogen, preferably over a period of 1 week or more.

In a preferable embodiment, the skin tissue is from a mouse, rat or human.

In a different aspect, the present invention provides a composition for regenerating hair follicles comprising: hair dermal papilla cell and epidermal cells; wherein, the ratio of the number of hair dermal papilla cell to the number of epidermal cells is from 1:10 to 10:1.

More preferably, the present invention provides a composition for regenerating hair follicles comprising a hair dermal papilla cell preparation and epidermal cells; wherein, said preparation is prepared by providing a cell suspension by removing epidermal tissue from skin tissue and subjecting the resulting dermal tissue fraction to collagenase treatment, and then cryopreserving the cell suspension to kill the follicular epidermal cells, in which the ratio of the number of hair dermal papilla cell to the number of epidermal cells is from 1:10 to 10:1.

Preferably, the ratio of the number of the hair dermal papilla cell to the number of the epidermal cells is from 1:3 to 10:1, more preferably from 1:1 to 10:1, even more preferably from 1:1 to 3:1, and most preferably 1:1.

Moreover, the present invention provides a method for regenerating hair follicles in an animal or three-dimensional skin equivalent using the aforementioned composition, and an animal or three-dimensional skin equivalent in which hair follicles have been regenerated in this manner.

According to the present invention, a method is provided for easily preparing a hair dermal papilla cell preparation that contains only hair dermal papilla cell as the active cellular component without using a transgenic mouse. This hair dermal papilla cell preparation can be used in transplant surgery for regenerating hair follicles and in research and development on follicle reconstitution. Since the hair dermal papilla cell preparation is free of contamination of active epithelial stem cells, it is particularly advantageous in situations requiring the ratio of the number of active hair dermal papilla cell and the number of active epithelial stem cells used for follicle regeneration to be precisely adjusted as well as requiring a large number of cells.

BRIEF DESCRIPTION OF THE DRAWINGS

FIG. 3 shows the results of follicle regeneration by a mixed transplant of frozen/thawed hair dermal papilla cell and epidermal cells.

FIG. 5 shows the results of Hoechst nuclear staining of follicle reconstitution in the case of using hair dermal papilla cell and epidermal cells derived from different species (rat-human system)

FIG. 6 shows the formation of primordial hair follicles in the case of having transplanted a follicle regeneration system of the present invention into a three-dimensional skin equivalent.

BEST MODE FOR CARRYING OUT THE INVENTION

Figure 1:
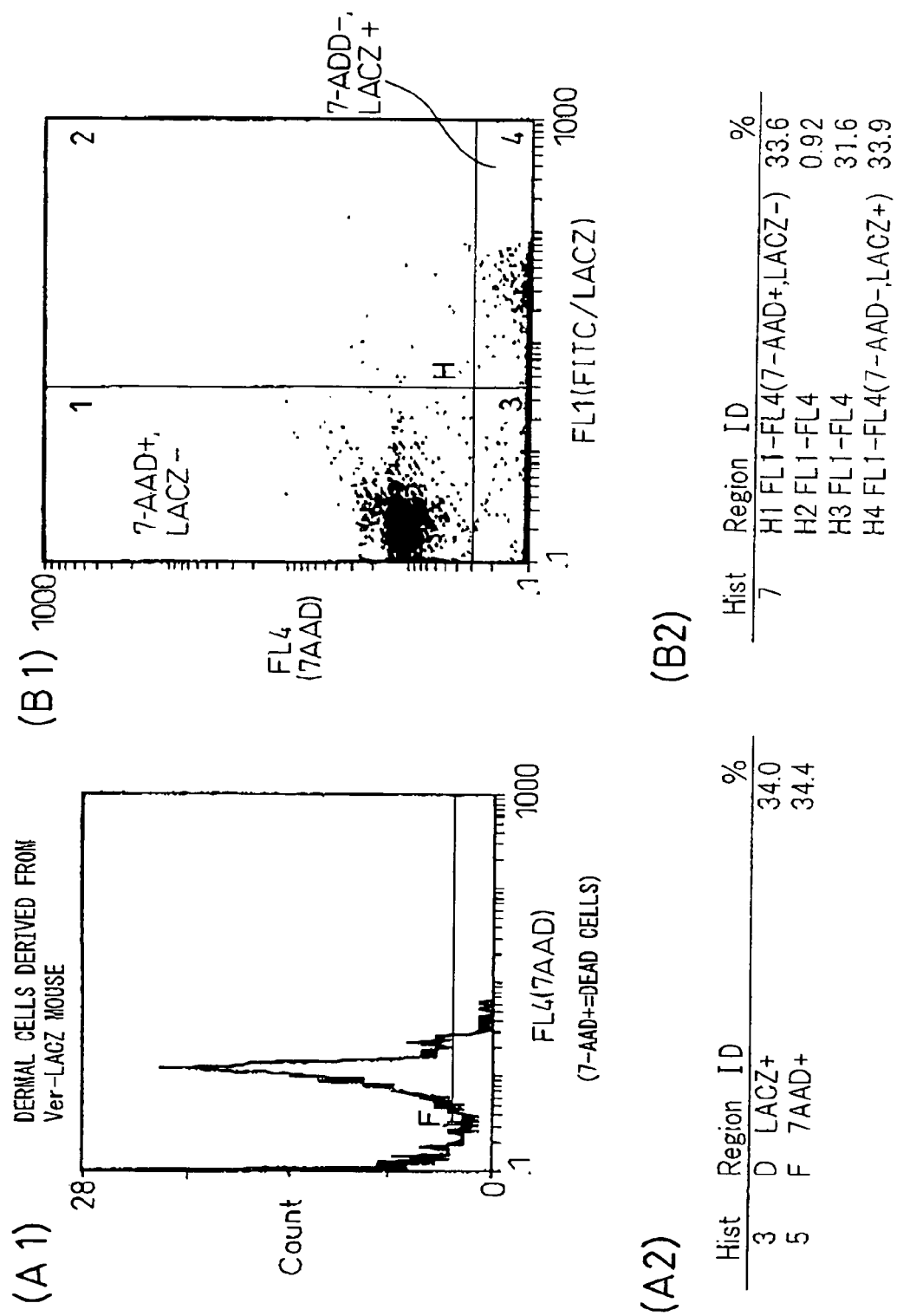
FIG. 1 shows the results of FACS analysis of a frozen/thawed dermal cell fraction based on LacZ and 7-AAD.

The present invention provides a method for preparing a hair dermal papilla cell preparation.

In addition, the present invention provides a composition containing hair dermal papilla cell and epidermal cells for regenerating hair follicles, a method for regenerating hair follicles using the same, and an animal or three-dimensional skin equivalent having hair follicles regenerated in such a manner.

"Hair dermal papilla cell" refer to cells located at the bottom of hair follicles in the form of mesenchymal cells that fulfill the role of a so-called control tower by sending out activation signals to follicular epithelial stem cells for self-regeneration of hair follicles. A hair dermal papilla cell preparation containing only active hair dermal papilla cell can be prepared according to, for example, the method of Kishimoto et al. (op. cit.) using transgenic mice. With respect to yield, however, it is preferable to, for example, remove epidermal tissue from the skin tissue to prepare a cell suspension by subjecting the resulting dermal tissue fraction to collagenase treatment, followed by cryopreserving the cell suspension to kill the follicular epidermal cells.

The method as claimed in the present invention using the aforementioned cryopreservation can be specifically carried out, for example, in the manner described below.

1. Mammalian epidermis is prepared.
2. This skin is allowed to stand undisturbed for a suitable amount of time, such as overnight, in a protease solution such as a trypsin solution as necessary, followed by removing the epidermal portion with a tweezers and so forth, and treating the remain dermis with collagen to prepare a cell suspension.
3. The suspension is filtered through a cell strainer as necessary to remove the sediment by allowing to stand undisturbed.
4. The number of cells is counted and then re-suspended in a cryopreserving liquid at a suitable cell density of preferably about $1\times10^5$ to $1\times10^8$/ml, the suspension is then divided into smaller aliquots as necessary, and then cryopreserved in accordance with ordinary cell storage methods.
5. The frozen suspension is then thawed after a suitable storage period and used.

Although there are no particular limitations on the cryopreserving method, the suspension is stored in an ultra-low-temperature freezer or in liquid nitrogen at $-20°$ C. or lower, preferably $-50°$ C. or lower, and more preferably $-80°$ C. or lower. Although there are also no particular limitations on the cryopreservation period, it is, for example, 1 day or more, preferably 3 days or more, and more preferably 1 week or more so as to destroy the epidermal cells. Furthermore, hair dermal papilla cell have been confirmed to continue to survive even after being stored for 4 months in liquid nitrogen. Conventional storage liquids used for the storage of cells, such as the Cell Banker 2 Cell Cryopreservation Liquid (Catalog No. BLC-2, Nippon Zenyaku Kogyo), can be used as the preservating liquid.

Cells can be counted by a method known among persons with ordinary skill in the art. For example, cells can be counted by placing a cell suspension diluted with an equal volume of 0.4% Trypan Blue stain (No. 15250-061, Invitrogen) on a hemocytometer (Eosinophil Counter, SLGC) and calculating the number of cells according to the method described in the instruction manual provided with the hemocytometer.

The mammalian skin serving as the source of hair dermal papilla cell used in the present invention may be from any mammal without limitation, examples of which include humans, chimpanzees and other primates, domestic animals such as dogs, cats, rabbits, horses, sheep, goats, cows and pigs, and laboratory test animals such as rats, mice and guinea pigs, and preferably nude mice, SCID mice and nude rats. In addition, there are no limitations on the animal strain.

The "epidermal cells" in the composition for regenerating hair follicles as claimed in the present invention are cells that compose the majority of the epidermis or epithelium of the skin, and arise from a single layer of basal cells in contact with the dermis. For example, in mouse, although epidermal cells originating in a newborn (or fetus) can be used preferably for the epidermal cells, they may also be cells originating in the epidermis of mature skin such as the epidermis of dormant hair, cells originating in the epidermis of growing hair, or a culture of cells in the keratinocyte state. Such cells can be prepared from the skin of a desired donor animal according to methods known among persons with ordinary skill in the art.

In a preferable aspect thereof, the epidermal cells can be prepared in the following manner.
1. Mammalian skin tissue is prepared.
2. This epidermis is treated with trypsin as necessary by allowing to stand overnight at 4° C. in 0.25% trypsin/PBS.
3. After separating only the epidermal portion with a tweezers and so forth and cutting into sections, the sections are suspended for about 1 hour at 4° C. in a suitable culture medium (such as keratinocyte culture liquid).
4. This suspension is passed through a cell strainer having a suitable pore size following by applying to a centrifuge to recover the epidermal cells.
5. This cell preparation is then suspended to a desired cell density in KGM or SFM medium and kept on ice until just prior to use.

Similar to the aforementioned hair dermal papilla cell, the epidermal cells of the present invention may originate in the skin of all mammals, examples of which include humans, chimpanzees and other primates, domestic animals such as dogs, cats, rabbits, horses, sheep, goats, cows and pigs, and laboratory test animals such as rats, mice and guinea pigs, and preferably nude mice, SCID mice and nude rats. In addition, the site of the epidermis may be a pilose site such as the scalp or a glabrous site such as the foreskin.

When the inventors of the present invention mixed a hair dermal papilla cell preparation containing only hair dermal papilla cell as the active cells and in which epidermal cells were killed, which was obtained according to the aforementioned cryopreservation, with an epithelial cell preparation containing only active epidermal cells from which dermal cells had been removed, at various cell ratios, and the mixtures were transplanted into recipient animals to examine regeneration of hair follicles, there was found to be a constant relationship between the ratio of the number of hair dermal papilla cell to the number of epidermal cells and the regeneration of hair follicles. Namely, in the case of desiring regeneration of more hair follicles, it was found that the ratio of the number of active hair dermal papilla cell to the number of active epidermal cells should be 1:3 to 10:1, preferably 1:1 to 10:1, more preferably 1:1 to 3:1, and most preferably 1:1. In other words, regeneration of hair follicles can be adjusted by. suitably adjusting the ratio of the number of active hair dermal papilla cell to the number of active epidermal cells and transplanting into a recipient animal.

Hair dermal papilla cell and epidermal cells may be combined from the same species or different species. For example, in the case of a hair dermal papilla cell preparation originating in mice, the epidermal cells may originate in mice (homologous) or they may originate in another species such as rats or humans (heterologous). Thus, a composition for regenerating hair follicles of the present invention may be a combination in which the hair dermal papilla cell and epidermal cells both originate in mice, a combination in which they both originate in rats, or a combination in which they both originate in humans (examples of homologous), or a combination in which the hair dermal papilla cell originate in mice while the epidermal cells originate in rice, a combination in which the hair dermal papilla cell originate in rats while the epidermal cells originate in mice, a combination in which the hair dermal papilla cell originate in mice while the epidermal cells originate in humans, a combination in which the hair dermal papilla cell originate in rats while the epidermal cells originate in humans, a combination in which the hair dermal papilla cell originate in humans while the epidermal cells originate in mice, or a combination in which the hair dermal papilla cell originate in humans while the epidermal cells originate in rats (examples of heterologous) The method for implanting a composition for regenerating hair follicles as claimed in the present invention can be carried out using a known transplant method, an example of which is described in Weinberg et al., J. Invest. Dermatol. Vol, 100 (1993), pp. 229-236. In the case of transplanting into nude mice, for example, the prepared cells are mixed from immediately before to 1 hour before transplant, the culture liquid is removed by centrifugation (9000×g, 10 min.) to form a cell mass of about 50 to 100 μl followed by promptly injecting into a silicon dome-shaped chamber embedded in the skin on the backs of the nude mice. The chamber is carefully removed 1 week later, and the presence of hair formation at the transplant site can be observed macroscopically starting in the second week. Transplantation for the purpose of hair growth can be carried out in a similar manner in animals, including humans, and an appropriate method is suitably selected by the physician or veterinarian.

Transplantation is preferably carried out by, for example, transplanting to a circle area having a diameter of about 1 cm in a transplanted amount in which the number of hair dermal papilla cell is $1\times10^6$ to $1\times10^8$/cm$^2$, preferably $1.0\times10^7$ to $1.5\times10^7$/cm$^2$, and more preferably $1.27\times10^7$/cm$^2$.

In the case of transplanting the aforementioned composition into a recipient animal, the transplant may be a homologous transplant, namely an autotransplant, an isotransplant or allotransplant, or a heterologous transplant. In the case of a homologous transplant, the hair dermal papilla cell preparation and the epidermal cells are both of the same species as the recipient. In a heterologous transplant, either the hair dermal papilla cell preparation or the epidermal cells are of a different species from the recipient and the other is of the same species as the recipient, or both are of a different species from the recipient. Any animal may be used for the recipient, examples of which include humans, chimpanzees and other primates, domestic animals such as dogs, cats, rabbits, horses, sheep, goats, cows and pigs, and laboratory test animals such as rats, mice and guinea pigs, and preferably nude mice, SCID mice and nude rats.

In addition, a chimeric animal having regenerated hair follicles can be provided by transplanting the aforementioned composition as claimed in the present invention into a suitable recipient animal. This animal can serve as a valuable animal model for researching and elucidating the mechanism of hair follicle regeneration or for screening for pharmaceuticals and herbal medicines effective for hair follicle regeneration, hair growth or hair removal. The recipient animal is preferably an immunosuppressed animal irrespective of the source of each cell contained in the system transplanted into the animal. In addition, any animal species used as a laboratory test animals may be used, provided that it coincides with the object of the present invention, examples of which include mice and rats. Among these animals, examples of animals having a suppressed immune system in the case of mice include those having a trait such as a missing thymus gland in the manner of nude mice. Furthermore, in consideration of the object of the present invention, particularly preferable examples of recipient animals include commercially available nude mice (e.g., Balb-c nu/nu strain), SCID mice (e.g., Balb/c-SCID strain) and nude rats (e.g., F344/N Jcl-rnu).

Moreover, a three-dimensional skin equivalent having regenerated hair follicles can be provided by incorporating the composition as claimed in the present invention in a three-dimensional skin equivalent. A three-dimensional skin equivalent can be produced, for example, in the manner described below according to methods known among persons with ordinary skill in the art (Exp. Cell Res., Amano S. et al., (2001), Vol. 271, pp. 249-262). The three-dimensional skin equivalent contains $1 \times 10^6$ to $1 \times 10^8$ hair dermal papilla cell/cm$^2$, preferably $1.0 \times 10^7$ to $1.5 \times 10^7$/cm$^2$, and more preferably about $1.27 \times 10^7$/cm$^2$.

Production Method of Three-Dimensional Skin Equivalent

Human fibroblasts are dispersed in a suitable amount of a mixture of 0.1% collagen solution, DMEM and 10% FBS, transferred to a Petri dish, and immediately allowed to stand undisturbed in a $CO_2$ incubator at 37° C. After gelling, the gel is scraped from the sides and bottom of the Petri dish so as to suspend in the Petri dish. It was cultured with shaking, and a dermis equivalent was obtained when the gel contracts to approximately one fifths of the size. The dermis equivalent is placed on a stainless steel grid, a glass ring is placed thereon, and 0.4 ml of cultured human epidermal cells ($1.0 \times 10^6$ cells/ml) dispersed in KGM (epidermal cell culture medium) are injected into the glass ring and cultured. At this time, a dermal cell fraction is simultaneously mixed and injected. Newborn mouse epidermal cells can also be used instead of human cultured epidermal cells. Medium consisting of DMEM, KGB and 5% FBS+$Ca^{2+}$ is added to the Petri dish so that the upper portion of the dermis equivalent is exposed to air followed by culturing. The dermis equivalent is observed after about one week and assessed for the presence of primordial follicle formation and reproducibility.

Similar to the aforementioned chimeric animal having regenerated hair follicles, this three-dimensional skin equivalent having reorganized hair follicles can be used for research and elucidation of the mechanism of hair follicle regeneration as well as screening for pharmaceuticals and herbal medicines effective for hair growth and hair removal.

The following provides a more detailed explanation of the present invention through examples thereof.

EXAMPLE 1

In order to confirm that epidermal cells die as a result of cryopreservation of a dermal cell fraction, and that a cell preparation containing only hair dermal papilla cell as the active cells is obtained as a result thereof, a cell fraction obtained from skin tissue collected from transgenic mice, in which an expression vector linked to a structural gene of LacZ marker protein was inserted downstream from a versican promoter (to be referred to as Versican-LacZ TG mice), was placed in cryopreservation followed by analysis of the thawed cell preparation by flow cytometry.

(1) Preparation of Cryopreserved Hair Dermal Papilla Cell Preparation from Dermal Cells of Versican-LacZ TG Mice (1-1) Individuals positive for LacZ were selected from the newborns (used within 4 days after birth) of the Versican-LacZ TG mice. Versican-LacZ TG mice can be produced according to, for example, the method described in Kishimoto et al. (op. cit.).

(1-2) After washing each individual with ethanol and phosphate-buffered physiological saline (abbreviated as "PBS"), the skin of the back was removed and allowed to stand overnight at 4° C. in a mixture of 0.25% trypsin and PBS.

(1-3) On the following day, the epidermis and dermis were separated with a tweezers, and the dermis portion was treated for about 1 hour at 37° C. with a mixture of 0.35% collagenase and DMEM (Dulbecco's Modified Eagle's Medium).

(1-4) After carefully suspending the cells obtained in (1-3), the suspension was passed through a cell strainer followed by collecting the cells with a centrifuge (900×g, 10 minutes).

(1-5) The number of cells was counted, the cells were re-suspended in cell cryopreservating liquid (Cell Banker 2 (BLC-2), Nippon Zenyaku Kogyo), transferred to a cryo-preservating tube and then stored in liquid nitrogen in accordance with conventional cell storage methods.

(1-6) The frozen cells were thawed after about one week and then used in the flow cytometry analysis described below.

(2) FluoroReporter LacZ Flow Cytometry Analysis Materials

FluoroReporter LacZ Flow Cytometry Kit (Molecular Probe, Catalog No. F-1930 (50 reactions)/F-1931 (250 reactions))

Reagent Preparation:

Reaction liquid: The FDG reagent contained in the kit (Component A) was diluted 1:10 with MiliQ water. 50 µl were used per sample.

Quencher: The PI reagent contained in the kit (Component D) was diluted 1:100 with the buffer provided with the kit. 0.9 ml were used per sample. The quencher was chilled at 4° C. on ice until the time of use. The staining media consisted of CD49f monoclonal antibody (Serotec), which is a specific antibody that specifically stains epidermal cells, and 7-ADD (Beckman-Coulter, PN-IM 3422), which specifically stains dead cells.

(2-1) The suspension of dermal cells from the Versican-LacZ TG mice was adjusted to $1 \times 10^7$ cells followed by the addition of 750 µl of staining media and transferred to a 1.5 ml Eppendorf tube.

(2-2) The cell suspension was centrifuged for 5 minutes for 3000 revolutions and the supernatant was discarded. The cell pellet was re-suspended in 100 AL of staining media. This suspension was pre-incubated for 10 minutes in a constant temperature bath at 37° C.

(2-3) 50 µL of reaction liquid that had been pre-incubated for 10 minutes in a constant temperature bath at 37° C. were then added and the reaction was carried out at 37° C. for exactly 1 minute.

(2-4) 0.9 ml of quencher were added after which the suspension was stored in ice.

(2-5) 10 minutes later, 40 µL of 50 MM PETG (component B) were added to completely inhibit the reaction.

(2-6) The fluorescence intensity of the cell suspension was promptly measured with the FACS. The operating procedure of the flow cytometer (FACS) was in accordance with the manufacturer's instruction manual. The XL-MCL manufactured by Beckman-Coulter, for example, can be used for the FACS measuring apparatus. The distribution of fluorescence intensity of the cells was measured using a detection setting suitable for the fluorescein used in this kit.

(3) Analysis Results

Figure 2:
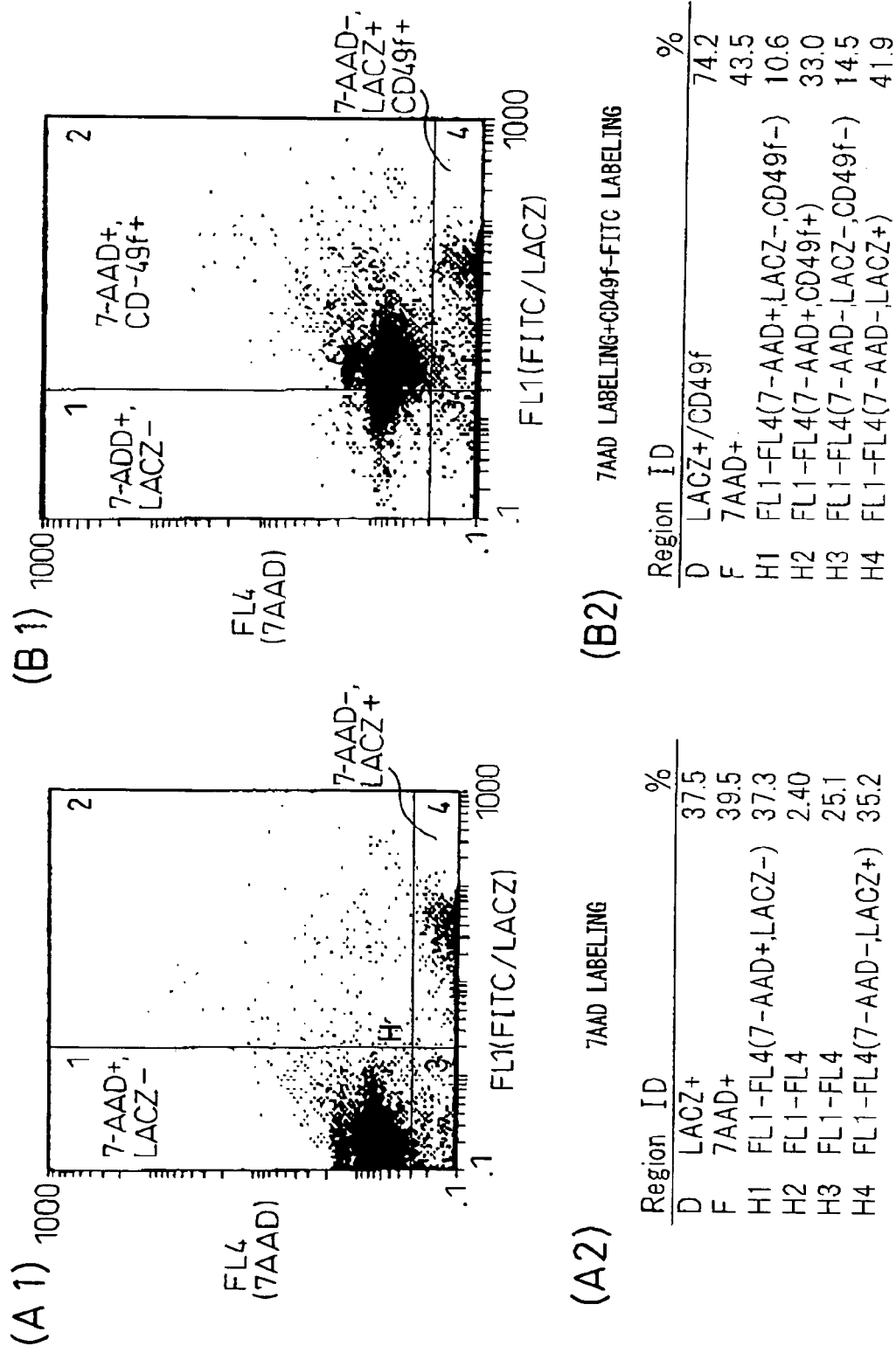
FIG. 2 shows the results of FACS analysis of a frozen/thawed dermal cell fraction based on CD-49 and 7-AAD.

FACS analysis based on LacZ and 7-AAD indicated that the majority of the LacZ+cells among the cryopreserved cells were viable cells even after cryopreservation (FIG. 1). Thus, hair dermal papilla cell are clearly not killed by cryopreservation. In addition, FACS analysis based on CD-49 and 7-AAD indicated that the majority of the CD-49$^+$ cells (epidermal cells) were present in the 7-AAD$^+$ fraction (dead cell fraction) after thawing (FIG. 2). Thus, the viable cells in the thawed cell preparation were LacZ$^+$, CD-49$^-$ and 7-AAD$^-$, namely hair dermal papilla cell (LacZ$^+$) and non-epidermal cells (CD-49$^-$), and were viable cells (7-AAD$^-$). In summary of these results, it was clear that the majority of the viable cells were not epidermal cells, but rather hair dermal papilla cell. Accordingly, it was also clearly demonstrated that epidermal cells can be specifically killed by freezing/thawing, and that a hair dermal papilla cell preparation can be prepared that contains only hair dermal papilla cell as the active cells.

EXAMPLE 2

Hair follicles were attempted to be regenerated by transplanting a mixture of frozen/thawed hair dermal papilla cell and epidermal cells.

I. Cell Preparation (1) Mouse Epidermal Cells
(1-1) Each individual selected from newborn ICR strain mice was washed with ethanol and phosphate-buffered physiological saline (abbreviated as "PBS") on the day before surgery followed by removal of skin from the back and treating the skin with trypsin by allowing to stand undisturbed overnight at 4° C. in a mixture of 0.25% trypsin and PBS.
(1-2) After peeling off only the epidermis portion with a tweezers and cutting into sections, the epidermis was suspended for about 1 hour at 4° C. in keratinocyte culture liquid (referred to as "KGM").
(1-3) The suspension of (1-2) was passed through a cell strainer and centrifuged (900×g, 10 minutes) to recover the epidermal cells.
(1-4) An amount of epidermal cells equivalent to two newborns were used for surgery for each recipient animal (cell count of about 1×10$^7$ cells). An equivalent amount of cells were suspended in KGF or SFM medium and allowed to stand undisturbed on ice until the time of use. This was designated as the "mouse epithelial cell preparation".

(2) Preparation of "Fresh" Mouse Dermal Cell Preparation

Comparative Example (2-1) Skin from the newborns of ICR strain mice was treated with trypsin in the same manner as the aforementioned (1-1) and (1-2) above on the day before surgery.
(2-2) After peeling off the epidermis portion with tweezers and cutting the remaining dermis into sections, the dermis was suspended and treated for about 1 hour at 37° C. in a suitable culture liquid of DMEM and 10% FBS containing 0.35% collagenase.

(2-3) The suspension of (2-2) was passed through a cell strainer and centrifuged to recover the dermal cells.
(2-4) About 1×10$^7$ dermal cells in terms of the cell count were used for surgery for each recipient animal.
An equivalent amount of cells were suspended in a mixture of OMEM and 10% FSS and so forth, and the suspension was allowed to stand undisturbed on ice until the time of use. This suspension was designated as "fresh mouse dermal cell preparation".

(3) Preparation of "Cryopreserved" Mouse Dermal Cell Preparation Containing Dermal Cell Fraction (3-1) Skin from the backs of newborn ICR strain mice was removed to collect the epidermis.
(3-2) After allowing to stand undisturbed overnight in trypsin solution, the epidermis was removed with a tweezers on the following day and the remaining dermis was treated with collagenase to prepare a cell suspension.
(3-3) The sediment was removed by filtering the suspension with a cell strainer and allowing to stand.
(3-4) After counting the number of cells, the cells were re-suspended in cryopreserving liquid to a cell density of 1×10$^5$ to 1×10$^8$/ml, the suspension was transferred to freezing tubes and then stored in liquid nitrogen according to conventional cell storage methods.
(3-5) The suspension was thawed about one week later and 1×10$^7$ cells/transplant were used in the transplant experiment. This was designated as the "cryopreserved" mouse dermal cell preparation.

II. Hair Follicle Reconstitution Method (Method for Transplanting to Animals)

The aforementioned mouse epithelial cell preparation of (1-4) was mixed with either the "fresh" mouse dermal cell preparation of (2-4) or the "cryopreserved" mouse dermal cell preparation of (3-5). These mixtures were used as cell suspensions in the reorganized hair follicle production procedure described below.
<Reorganized Hair Follicle Production Procedure>
Materials:
Recipient animals (Balb-c nu/nu strain nude mice, age 5 weeks or older),
silicon dome-shaped cap having a diameter of about 1 centimeter (to be referred to as "bulb"),
anesthetic,
surgical scissors, tweezers, suture,
micropipetter, and
cell suspensions (suspended in about 150 μl of a mixture of DMEM-culture liquid and 10% FBS).
<Procedure>
(i) The nude mice were anesthetized.
(ii) Skin was cut away from the back over an area of just under 1 centimeter in diameter.
(iii) The bulb was inserted into the wound opening and fastened with the suture.
(iv) A cell suspension was injected into the bulb using the pipetter.
(v) The animals were housed for about 1 week in this state followed by removal of the bulb.
(vi) After having removed the bulb, the growth of reorganized hair follicles was observed at the scar where the scab had come off about 1 to 6 weeks later (normally after 2 weeks).
The results of the hair follicle reconstitution experiment are shown in Table 1 and FIG. 3. In contrast to regeneration of hair follicles being observed even in the case of transplanting only the "fresh" mouse dermal cell preparation, regeneration of hair follicles was not observed in the case of transplanting only the "cryopreserved" mouse dermal cell preparation. These results agree with the results obtained by Kishimoto et al. (op. cit.) using hair dermal papilla cell purified with a cell sorter from a dermal cell fraction originating in transgenic mice, and verified that only hair dermal papilla cell are contained as active cells in the "cryopreserved" mouse dermal cell preparation".

TABLE 1

| Dermal cell fraction | Epithelial cell fraction | Hair follicle regeneration | (No. of hairs/no. of transplants) |
|---|---|---|---|
| Fresh (not frozen) | Fresh | ++ | (4/4) |
| Fresh (not frozen) | -- | ++ | (4/4) |
| Frozen/thawed | Fresh | ++ | (10/10) |
| Frozen/thawed | -- | -- | (0/10) |
| -- | Fresh | -- | (0/10) |

EXAMPLE 3

Effect of Cell Ratio of Papilla Cell Fraction and Epithelial Cell Fraction on Hair Follicle Reconstitution Efficiency A "cryopreserved" mouse dermal cell preparation and epidermal cells originating in the skin of newborn rats prepared using the same treatment as the mouse epidermal cells described in Example 2 were respectively adjusted to cell counts of $0.1 \times 10^6$, $3.3 \times 10^6$ and $1 \times 10^7$ cells and then mixed. The mixtures were transplanted into skin on the back of nude mice according to the reorganized hair follicle production procedure previously described to investigate the presence of hair follicle reconstitution. Those results are shown in Table 2 below.

TABLE 2

Effects of Cell Ratio of Dermal Cell Fraction and Epithelial Cell Fraction on Hair Follicle Reconstitution Efficiency

| Dermal cell fraction | Epithelial cell fraction | Hair follicle regeneration |
|---|---|---|
| 0 | $1.0 \times 10^7$ | – |
| $1.0 \times 10^6$ | $1.0 \times 10^7$ | ± |
| $3.3 \times 10^6$ | $1.0 \times 10^7$ | + |
| $1.0 \times 10^7$ | $1.0 \times 10^7$ | +++ |
| $1.0 \times 10^7$ | $3.3 \times 10^6$ | +++ |
| $1.0 \times 10^7$ | $1.0 \times 10^6$ | ++ |
| $1.0 \times 10^7$ | 0 | – |

According to the results of Table 2, hair follicle regeneration was observed when the mixing ratio of hair dermal papilla cell and epidermal cells was within the range of 1:10 to 10:1, and when cell mixtures having a ratio of 1:1 to 3:1, and particularly about 1:1, were transplanted, hair follicle regeneration was determined to occur prominently.

EXAMPLE 4

Hair Follicle Reconstitution When Using Epidermal Cells Originating in Mature Mouse Skin Preparation of epidermal cells originating in mature mouse skin (mice age 10 weeks or older) was carried out in compliance with the preparation of newborn mouse epidermal cells described in Example 2. Two types of epidermal cells were used for the epidermal cells originating in mature mouse skin. These consisted of epidermal cells prepared from epidermis of dormant hair of mice age 10 weeks or older (mixture containing dormant hair epidermal cells), and epidermal cells prepared from the epidermis of mice in which hair growth was promoted (mixture containing active growth-induced hair epidermal cells). The epidermal cells originating in mature mouse skin were each mixed with a "cryopreserved" mouse dermal cell preparation so that the ratio of the number of cells was 1:1, and the mixtures were transplanted to the backs of mice according to the previously described reorganized hair follicle production procedure. Those results are shown in Table 3 below.

TABLE 3

| Dermal cell fraction | Epithelial cell fraction | Hair follicle reconstitution | (No. of primordial follicles formed/no. of transplants) |
|---|---|---|---|
| Mouse | Mouse (newborn epidermal cells) | + | (2/2) |
| Mouse | Mouse (mature mice: dormant) | ++ | (3/3) |
| Mouse | Mouse (mature mice: active) | ++ | (3/3) |

+++: High-density hair growth observed
++: Hair growth observed
+: Follicle formation observed in transplanted tissue The presence or absence of the formation of primordial hair follicles was evaluated by preparing thin As is clear from these results, hair growth was observed in both the case of transplanting the mixture containing dormant hair epidermal cells and the mixture containing active growth-induced epidermal cells. Thus, the present invention was determined to be effective for hair follicle regeneration not only in the case of the epidermal cells originating in newborn epidermis, but also in the cases of originating in mature epidermis such as the epidermis of dormant hair or actively growing hair.

EXAMPLE 5

Figure 4:
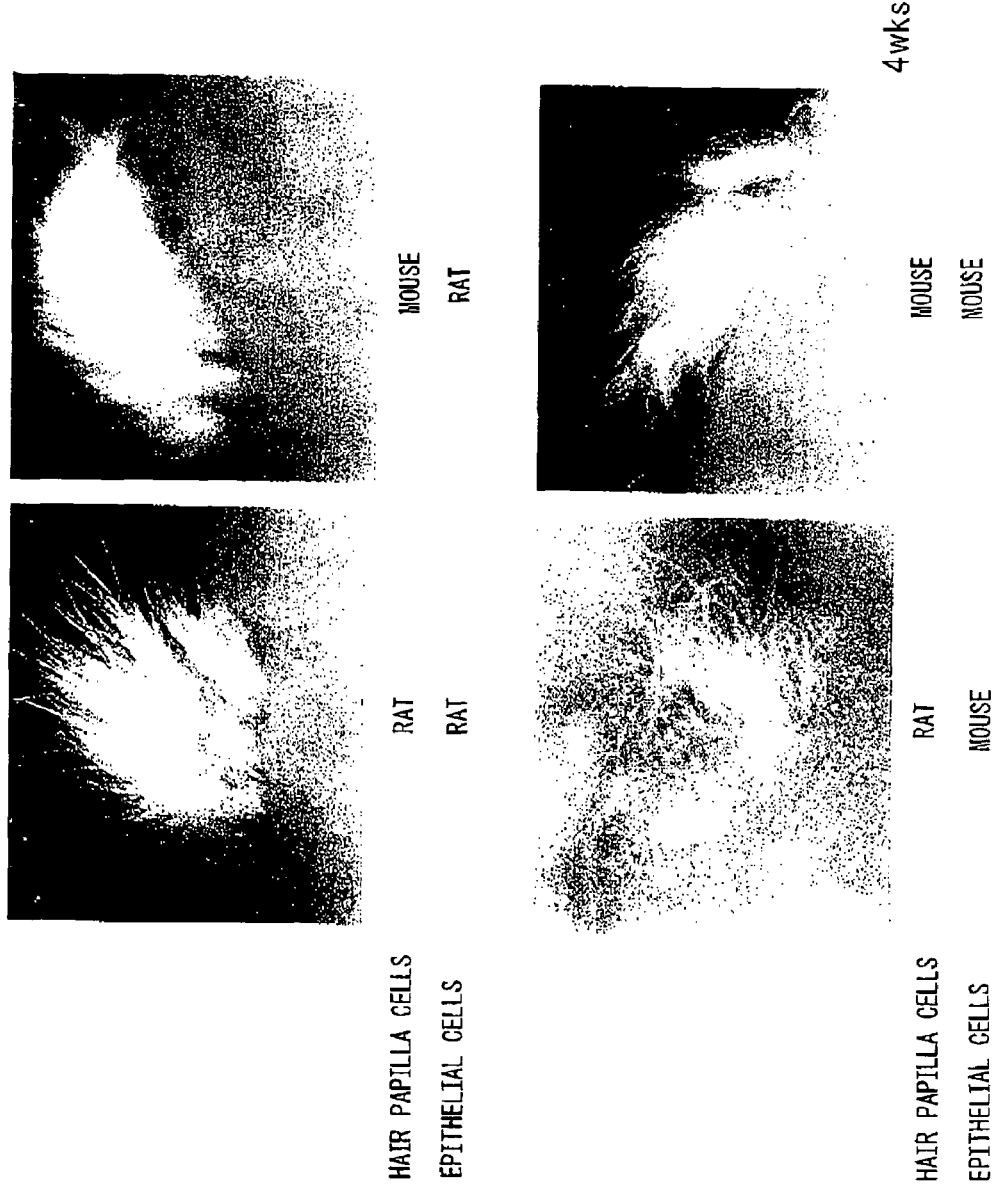
FIG. 4 shows the results of follicle reconstitution in the case of using hair dermal papilla cell and epidermal cells derived from different species (mouse-rat system).

Hair Follicle Reconstitution When Using Different Species of Hair dermal papilla cell and Epidermal Cells A "cryopreserved" mouse dermal cell preparation and epidermal cells originating in the skin of newborn rats mixed at about $1 \times 10^7$ cells each, and the reconstitution of hair follicles was investigated by transplanting into the skin on the backs of nude mice according to the previously described reorganized hair follicle production procedure. Those results are shown below in Table 4 and in FIG. 4.

TABLE 4

| Dermal cell fraction | Epithelial cell fraction | Hair follicle reconstitution | No. of primordial follicles formed/no. of transplants |
|---|---|---|---|
| Mouse | Mouse (newborn) | +++ | (12/12) |
| Rat | Rat (newborn) | +++ | (3/3) |
| Mouse | Rat (newborn) | +++ | (4/4) |

+++: High-density hair growth observed
++: Hair growth observed
+: Follicle formation observed in transplanted tissue As is clear from these results, the present invention was determined to be effective for regenerating hair follicles even if the mixture of hair dermal papilla cell and epidermal cells consists of cells from different species, and the effects are the same as when using cells from the same species.

EXAMPLE 6

Hair Follicle Reconstitution When Using Epidermal Cells originating in Human Newborn Foreskin Epidermal cells were prepared from human newborn foreskin obtained by circumcision and so forth and mixed with a cryopreserved mouse hair dermal papilla cell preparation followed by investigating for the presence of hair follicle reconstitution by transplanting the mixture into skin on the backs of nude mice according to the previously described reorganized hair follicle production method.

Foreskin tissue can be stored for approximately 1 to 3 weeks by placing in a refrigerator in a conventional fibroblast culture medium (such as DMEM) and keratinocyte culture medium (such as keratinocyte SMF medium, Invitrogen).

Cell cultures derived from foreskin were prepared in the manner described below.

The foreskin tissue in the aforementioned media (which can be used regardless of race) was allowed to react for 30 minutes in a Petri dish filled with a solution to which an antibiotic such as streptomycin or penicillin had been added to PBS (for tissue culturing, calcium and magnesium-free). The tissue was further allowed to react for 10 minutes after transferring to a Petri dish filled with fresh PBS and antibiotic. After removing excess fat tissue, the tissue was cut into skin sections of about 1 cm$^2$ and allowed to react for about 18 hours at 4° C. while suspended in Dispase solution (Godo Seishu Co., concentration: 1000 to 5000 U). After reacting, the epithelium portion was grabbed and peeled off with a tweezers after having washed again with PBS. The removed epithelium sheet was suspended in 5 ml of 0.5 mM EDTA solution containing 0.05% trypsin and allowed to react for 15 minutes at 37° C.

After stopping the reaction by adding trypsin inhibitor, the suspension was centrifuged for 10 minutes and 900 revolutions followed by discarding the supernatant. The pellet was re-suspended in 10 ml of keratinocyte SFM medium (Invitrogen) and the number of cells was counted. About $1\times10^6$ to $1\times10^7$ cells were used for a single transplant experiment. In the case of preparing subcultured epidermal cells for transplant, about $1\times10^6$ epidermal cells were seeded in a 100 mm Petri dish or 75 cm$^2$ flask coated with type I or type IV collagen solution, and cultured according to conventional methods in a $CO_2$ incubator using keratinocyte SFM medium. Once the cells had reached confluence, the cells were separated with trypsin, collected and again prepared to a cell density of $1\times10^6$ followed by subculture until the required number of cells or passage was reached.

The results of the above transplants are shown in Table 5 below.

TABLE 5

| Dermal cell fraction | Epithelial cell fraction | Hair follicle reconstitution | (No. of primordial follicles formed/ no. of transplants) |
|---|---|---|---|
| Mouse | Human (newborn foreskin) | + | (3/3) |
| Mouse | Human (newborn foreskin cultured cells) | + | (2/2) |

TABLE 5-continued

| Dermal cell fraction | Epithelial cell fraction | Hair follicle reconstitution | (No. of primordial follicles formed/ no. of transplants) |
|---|---|---|---|

+: Hair follicle formation observed in transplant tissue

It was determined from these results that the present invention is effective for regeneration of hair follicles even if epidermal cells of human origin are combined with mouse hair dermal papilla cell. In addition, it is interesting to note that foreskin cells resulted in regeneration of hair follicles when combined with hair dermal papilla cell even though they are epidermal cells originating at skin location that does not have hair follicles or hair roots. Thus, it was clearly demonstrated that epidermal cells capable of being combined with hair dermal papilla cell in hair follicle regeneration systems are not limited to those from pilose sites, but also from glabrous skin sites as well.

EXAMPLE 7

Hair Follicle Reconstitution When Using Epidermal Cells Originating in Human Adult Foreskin Epidermal cells were prepared from adult foreskin tissue (age 20) obtained by phimosiectomy and so forth and mixed with a cryopreserved mouse hair dermal papilla cell preparation followed by investigating for the presence of hair follicle reconstitution by transplanting the mixture into skin on the backs of nude mice according to the previously described reorganized hair follicle production method.

Adult foreskin tissue can be stored for about 1 week by placing in cryopreservation in a conventional fibroblast culture medium (such as DMEM) and keratinocyte culture medium (such as keratinocyte SMF medium, Invitrogen).

Preparation of cultured cells originating in adult foreskin tissue was carried out in compliance with the preparation method for newborn foreskin cultured cells of Example 6.

The results of the above transplants are shown in Table 6 below.

TABLE 6

| Dermal cell fraction | Epithelial cell fraction | Hair follicle reconstitution | (No. of primordial follicles formed/ no. of transplants) |
|---|---|---|---|
| Mouse | Human (adult foreskin) | + | (1/1) |
| Mouse | Human (adult foreskin cultured cells) | + | (4/6) |

+: Hair follicle formation observed in transplant tissue

It was determined from these results that the present invention is effective for regeneration of hair follicles even if epidermal cells of adult human origin are combined with mouse hair dermal papilla cell. This clearly demonstrated that epidermal cells capable of being combined with hair dermal papilla cell in hair follicle regeneration systems are not limited to those of the course of development but also of mature tissue.

EXAMPLE 8

Effects of Passage of Cultured Cells from Human Foreskin on Hair Follicle Reconstitution The results of assessing the efficiency of reconstitution are shown in Table 7 below in the case of combining epidermal cells from different races of human newborn or adult foreskin with varied numbers of passage in an experiment on hair follicle reconstitution.

TABLE 7

| Hair dermal papilla cell | Epidermal cells | Race | No. of subcultures | Hair follicle reorganization | (No. of primordial follicles/no. of transplants) |
|---|---|---|---|---|---|
| Mouse | Human (newborn foreskin) | Negro | 0 | + | (3/3) |
| Mouse | Human (newborn foreskin cultured cells) | Negro | 1 | + | (2/2) |
| Mouse | Human (newborn foreskin cultured cells) | Negro | 2 | + | (3/3) |
| Mouse | Human (newborn foreskin cultured cells) | Caucasian | 1 | + | (1/1) |
| Mouse | Human (newborn foreskin cultured cells) | Caucasian | 2 | + | (1/4) |
| Mouse | Human (newborn foreskin cultured cells) | Caucasian | 3 | − | (0/2) |
| Mouse | Human (newborn foreskin cultured cells) | Caucasian | 5 | − | (0/2) |
| Mouse | Human (adult foreskin cultured cells) | Japanese | 0 | + | (1/1) |
| Mouse | Human (adult foreskin cultured cells) | Japanese | 1 | + | (2/2) |
| Mouse | Human (adult foreskin cultured cells) | Japanese | 2 | + | (2/4) |
| Mouse | Human (adult foreskin cultured cells) | Japanese | 3 | + | (0/1) |

\* Hair follicle formation observed in transplant tissue
−: Hair follicle formation not observed in transplant tissue It was clearly demonstrated from these results that hair follicles are reorganized to a greater extent the fewer the number of subcultures of the epidermal cells regardless of race.

EXAMPLE 9

Study of Reorganized Hair Follicles

A method that uses, for example, species-specific antibodies or a species-specific gene sequence (such as human Alu sequence) can be used to confirm whether or not reorganized hair follicles are composed of combinations hair dermal papilla cell and epidermal cells. Most conveniently, this can be distinguished easily by histological observations using an heterologous type composition for regeneration of hair follicles as claimed in the present invention (e.g., using mouse hair dermal papilla cell and rat or human epidermal cells or the opposite) and staining with Hoechst #33258 reagent (Molecular Probe) used for nucleus staining (Miller G. J. and Ferrara J. A., Stain Technol. 63 (1): 15-21, 1988), by which a plurality of dots (points) being clearly observed in the nucleus in the case of murine while not being observed in humans and rats.

<Hoechst #33258 Nuclear Staining>

A paraffin section obtained by thinly slicing tissue from the transplant site was placed on a slide glass (preferably 4 to 6 μm thick), subjected to a conventional paraffin removal treatment (consisting of washing twice with xylene, washing with 99.9% ethanol, washing with 80% ethanol, washing with 70% ethanol and finally washing with water) and transferred to PBS solution (the section can be allowed to remain in this state for a short period of time).

4 mg of Hoechst #33258 (Molecular Probe) were dissolved in 1 mL of PBS solution (and blocked from light with aluminum foil). 10 μl of the resulting Hoechst #33258 solution were diluted with 10 ml of PBS (1000-fold dilution, final concentration: 4 μg/mL), and several drops were added to the tissue section on the horizontally positioned slide glass so as to completely cover the section. Subsequently, the solution was allowed to react for 15 minutes at room temperature while blocking from light, and after washing with water for 5 minutes, the slide glass was sealed with GVA Mounting Solution (glycerol-based sealant, Zymed Lab, available from Funakoshi Yakuhin) and a cover glass. The slide glass was observed with a fluorescent microscope allowing observation of excitation in the UV band.

According to this method, the nuclei of mouse cells appear bright and a plurality of dots are observed. Since dots are not visible in the other rat and human cells, the source species of the tissue can be distinguished.

FIG. 5 shows the results of a fluorescent micrograph in the case of having transplanted a hair follicle reconstitution system in which the hair dermal papilla cell originate in mice while the epidermal cells originate in humans (human newborn foreskin) in comparison with the image of tissue following conventional tissue staining, namely hematoxylin-eosin (HE) staining (Complete Reference to Staining Methods, Ishiyaku Publishing Co., Ltd., p. 2-7, 1988). It can be clearly seen from this figure that the hair follicles are composed both of hair dermal papilla cell (portions having large numbers of bright dots originating in mice) and epidermal cells (portions not having dots originating in humans).

EXAMPLE 10

Primordial Hair Follicle Regeneration in a Three-Dimensional Skin Equivalent Human fibroblasts were dispersed in a suitable amount of a mixture of 0.1% collagen solution, DMEM and 10% FBS, transferred to a Petri dish and immediately allowed to stand undisturbed in a $CO_2$ incubator at 37° C. After gelling, the gel was scraped from the sides and bottom of the Petri dish so as to float in the Petri dish. It was cultured with shaking, a dermis equivalent was obtained when the gel contracts to approximately one fifth of the size. The dermis equivalent was placed on a stainless steel grid, a glass ring was placed thereon, and 0.4 ml of cultured human epidermal cells ($1.0\times10^6$ cells/ml) dispersed in KGM (epidermal cell culture medium) were injected into the glass ring and cultured. At this time, a cryopreserved mouse dermal cell preparation was simultaneously mixed and injected. Medium consisting of DMEM, KGB and 5% FBS +$Ca^{2+}$ was added to the Petri dish so that the upper portion of the dermis equivalent was exposed to air followed by culturing. The dermis equivalent was observed after about one week and assessed for the presence of primordial follicle formation and reproducibility by hematoxylin-eosin staining and the aforementioned Hoechst staining. Those results are shown in FIG. 6.

As is clear from the results of FIG. 6, primordial hair follicle formation was observed even when a hair follicle regeneration system as claimed in the present invention is transplanted into a three-dimensional skin equivalent.

INDUSTRIAL APPLICABILITY

A composition for regenerating hair follicles as claimed in the present invention can be used for transplanting hair follicles and research and development on hair follicle reconstitution.

The invention claimed is:

1. A composition comprising a hair dermal papilla cell preparation and epidermal cells, wherein the hair dermal cell preparation is prepared by a method comprising:
    (a) providing a skin tissue;
    (b) removing epidermal tissue from the skin tissue, thereby producing a dermal tissue fraction;
    (c) subjecting the dermal tissue fraction to collagenase treatment, thereby producing a cell suspension comprising hair dermal papilla cells; and
    (d) cryopreserving the cell suspension to kill follicular epidermal cells present in the cell suspension, thereby producing the hair dermal papilla cell preparation;
    wherein the composition is prepared by mixing the hair dermal papilla cell preparation with an amount of active epidermal cells to obtain a ratio of the number of hair dermal papilla cells to the number of active epidermal cells from 1:10 to 10:1, thereby producing the composition; and
    wherein the hair dermal papilla cells and the active epidermal cells are each obtained from a mammal selected from the group consisting of a mouse, a rat, and a human.

2. A composition according to claim 1, wherein the ratio of the number of hair dermal papilla cells to the number of epidermal cells is from 1:3 to 10:1.

3. A composition according to claim 1, wherein cryopreserving the cell suspension is carried out after adjusting the cell density of the cell suspension to $1\times10^5$ to $1\times10^8$ cells/ml.

4. A composition according to claim 1, wherein cryopreserving the cell suspension is carried out at a temperature of −80° C. or lower.

5. A composition according to claim 1, wherein cryopreserving the cell suspension is carried out in liquid nitrogen.

6. A composition according to claim 1, wherein cryopreserving the cell suspension is carried out for a period of 1 week or more.

7. The composition of claim 1, wherein the hair dermal papilla cells and the active epidermal cells both originate in mice, both originate in rats or both originate in humans.

8. The composition of claim 1, wherein the mammal for obtaining the hair dermal papilla cells and the mammal for obtaining the active epidermal cells are the same mammal, are different mammals of the same species, or are different species of mammals.

9. The composition of claim 1, wherein the active epidermal cells are obtained from human foreskin.

* * * * *